United States Patent
Tsujimoto

(10) Patent No.: US 9,320,579 B2
(45) Date of Patent: Apr. 26, 2016

(54) DENTAL MOLDED PRODUCT FOR MILLING AND MANUFACTUAL METHOD THEREOF

(75) Inventor: Masaya Tsujimoto, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 530 days.

(21) Appl. No.: 13/695,499

(22) PCT Filed: Jun. 22, 2011

(86) PCT No.: PCT/JP2011/064244
§ 371 (c)(1),
(2), (4) Date: Oct. 31, 2012

(87) PCT Pub. No.: WO2011/162286
PCT Pub. Date: Dec. 29, 2011

(65) Prior Publication Data
US 2013/0049241 A1    Feb. 28, 2013

(30) Foreign Application Priority Data

Jun. 25, 2010  (JP) ................. 2010-145385

(51) Int. Cl.
| A61C 13/087 | (2006.01) |
| A61C 13/08 | (2006.01) |
| A61K 6/083 | (2006.01) |
| A61K 6/08 | (2006.01) |
| C08L 33/10 | (2006.01) |
| A61C 13/00 | (2006.01) |
| A61C 13/01 | (2006.01) |

(52) U.S. Cl.
CPC ............ *A61C 13/0022* (2013.01); *A61C 13/01* (2013.01); *A61C 13/087* (2013.01); *A61K 6/083* (2013.01)

(58) Field of Classification Search
None
See application file for complete search history.

(56) References Cited

U.S. PATENT DOCUMENTS

| 5,708,051 | A | * | 1/1998 | Erdrich et al. ............... 523/116 |
| 5,990,195 | A |   | 11/1999 | Arita |
| 6,482,284 | B1 |   | 11/2002 | Reidt et al. |
| 6,627,327 | B2 |   | 9/2003 | Reidt et al. |
| 7,090,722 | B2 | * | 8/2006 | Budd et al. ..................... 106/35 |
| 8,436,078 | B2 | * | 5/2013 | Okubayashi et al. ......... 523/216 |
| 8,722,759 | B2 | * | 5/2014 | Craig ............................ 523/116 |
| 2003/0073394 | A1 |   | 4/2003 | Reidt et al. |
| 2005/0252415 | A1 | * | 11/2005 | Budd et al. ..................... 106/35 |
| 2011/0046260 | A1 | * | 2/2011 | Okubayashi et al. ......... 523/115 |
| 2011/0196062 | A1 | * | 8/2011 | Craig ............................ 523/116 |
| 2013/0049241 | A1 | * | 2/2013 | Tsujimoto ..................... 264/19 |

FOREIGN PATENT DOCUMENTS

| CN | 1130501 | 9/1996 |
| CN | 101224169 | 7/2008 |
| JP | 04-046303 | 2/1992 |
| JP | 2005-335237 | 12/2005 |
| JP | 2009-286784 | 12/2009 |
| WO | WO 2009133913 A1 * | 11/2009 ............ A61K 6/083 |
| WO | 2009/154301 | 12/2009 |

OTHER PUBLICATIONS

Basic Characteristics of AEROSIL fumed silica, Technical Bulletin Fine Particles 11, Nov. 1, 2006, pp. 1-44.*
Technical Bulletin 11, Basic Characteristics of AEROSIL fumed silica, Technical Bulletin Fine Particles 11, Nov. 1, 2006, pp. 1-44.*
Office Action issued Jul. 14, 2014 in CN 201180030688.2 with English translation thereof.
U.S. Appl. No. 13/640,768 to Masaya Tsujimoto et al., filed Oct. 12, 2012.
U.S. Appl. No. 13/640,773 to Masaya Tsujimoto et al., filed Oct. 12, 2012.
Search report from International Application No. PCT/JP2011/064244, mail date is Sep. 27, 2011.

* cited by examiner

*Primary Examiner* — Peter A Salamon
(74) *Attorney, Agent, or Firm* — Greenblum & Bernstein, P.L.C.

(57) ABSTRACT

Dental molded product for milling having excellent aesthetic quality, compatibility for machine and moldability from the moldable composition is provided. The dental molded product for milling is obtained by curing the moldable composition which includes a polymerizable monomer, a polymerization initiator, a first spherical inorganic filler and a second spherical inorganic filler. An average particle size of the first spherical inorganic filler is in the range of 0.2 to 10 μm. A content of the first spherical inorganic filler is in the range of 50 to 85 mass %. An average particle size of the second spherical inorganic filler is in the range of 0.005 to 0.1 μm. A content of the second spherical inorganic filler is in the range of 1 to 18 mass %.

5 Claims, No Drawings

DENTAL MOLDED PRODUCT FOR MILLING AND MANUFACTUAL METHOD THEREOF

TECHNICAL FIELD

The present invention relates to a dental molded product for milling which is used as dental crown material, prosthetic material and other dental molded product by performing the milling and a manufacturing method thereof.

BACKGROUND ART

In order to obtain the teeth crown material and prosthetic material such as dental crown or inray and the upper structures for provisional restoration or implant treatment, the molded product (the dental molded product) is used well-generally. Herein, the molded product is obtained by curing the moldable composition including the inorganic powder such as silica (silicon oxide), the polymerizable monomer such as (meth)acrylate, and the photo-polymerization initiator (or the heat-polymerization initiator).

In order to substitute from natural tooth, the dental molded product is required aesthetic quality, strength and permanence. Consequently, some kinds of materials are suggested. For example, it is disclosed to be obtained the dental prosthetic material such as inlay and crown by performing the milling to the dental resin material which consists of acrylic resin polymer including the inorganic filler in the range of 20 to 70 mass % and the glass powder in the range of 1 to 40 mass % in Patent Reference 1. Herein, the inorganic filler has an average particle size of 0.01 to 0.05 μm, and the glass powder has an average particle size of 0.1 to 5 μm.

PRIOR ART REFERENCE

Patent Reference

Patent Reference 1: Japan patent publication No. 10-323353

DISCLOSURE OF THE INVENTION

Problems to be Solved by the Invention

However, the composition disclosed in the Patent Reference 1 has a problem that the flowability of the moldable composition before polymerization is reduced significantly. This moldable composition has an irrelevant moldability. Additionally, there is a need of the molding under the high pressure in order to suppress an interfusion of bubbles within the polymer.

The present invention was made in view of the above circumstances, and an object thereof is to provide a dental molded product for milling having the excellent aesthetic quality, compatibility for machine and moldability from the moldable composition.

Means for Solving the Problems

A dental molded product for milling in the present invention is obtained by curing a moldable composition. wherein said moldable composition comprises: a polymerizable monomer, a polymerization initiator, a first spherical inorganic filler, and a second spherical inorganic filler. wherein said first spherical inorganic filler has an average particle size in the range of 0.2 to 10 μm and is included in a content of 50 to 85 mass %, and wherein said second spherical inorganic filler has an average particle size in the range of 0.005 to 0.1 μm and is included in a content of 1 to 18 mass %.

In the present invention, the polymerizable monomer preferably comprises a polyethylene glycol dimethacrylate in the range of 6 to 30 mass %, said polyethylene glycol dimethacrylate having a molecular weight in the range of 300 to 780.

In the present invention, the polymerizable monomer preferably comprises a triethylene glycol dimethacrylate in a content of 1 to 60 mass %.

The dental molded product for milling is provided by a manufacturing method including a step for preparing the moldable composition, a step for filling the moldable composition into the molding die, a step for removing bubbles within the moldable composition under the reducing pressure in the molding die, and a step for curing the moldable composition under the pressure of normal pressure to 40 MPa in the molding die.

Effect of the Invention

In the present invention, the dental molded product can be obtained from the moldable composition having a excellent aesthetic quality, compatibility for machine and flowability.

BEST MODE FOR CARRYING OUT THE INVENTION

The moldable composition to produce the dental molded product for milling includes the polymerizable monomer, the polymerization initiator, the first spherical inorganic filler and the second spherical inorganic filler.

Examples of the polymerizable monomer include a well known polymerizable monomer for general dental use such as (meth) acrylate monomer, urethane (meth) acrylate monomer and (meth) acrylate monomer having bispenol A skeleton.

The polymerizable monomer may include a general electric material. Herein, the electric material is a compound of epoxy resin monomer such as bisphenol A diglycidyl ether.

The polymerizable monomer preferably includes a polyethylene glycol dimethacrylate in the range of 6 to 30 mass %, and the polyethylene glycol dimethacrylate preferably has a molecular weight in the range of 300 to 780. When the polymerizable monomer includes at least 6 mass % of the polyethylene glycol dimethacrylate having the molecular weight of 300 to 780, the heat-curing reaction rate of the moldable composition is suppressed to low, and the hardening shrinkage at the molding is suppressed more. Additionally, When the polymerizable monomer includes not more than 30 mass % of the polyethylene glycol dimethacrylate having the molecular weight of 300 to 780, it is possible that the dental molded product for milling becomes to have high strength. More preferably, the polymerizable monomer includes the polyethylene glycol dimethacrylate in the range of 10 to 20 mass %, and the polyethylene glycol dimethacrylate has the molecular weight of 300 to 780.

As the polyethylene glycol dimethacrylate having the molecular weight of 300 to 780, one specie or multiple species may be selected, for example, from tetraethylene glycol dimethacrylate (molecular weight; 330), nonaethylene glycol dimethacrylate (molecular weight; 550), tetradecaethylene glycol dimethacrylate (molecular weight; 770).

when the polymerizable monomer includes the polyethylene glycol dimethacrylate in the range of 6 to 30 mass %; and the polyethylene glycol dimethacrylate has the molecular weight of 300 to 780, the dental molded product for milling in large size can be obtained easy because of suppressing the heat-curing reaction rate of the moldable composition to low, more suppressing the hardening shrinkage at the molding and becoming to have high strength in the dental molded product for milling as described above. In this case, it is possible to obtain the dental molded product for milling which has a volume of 20 to 350 cm$^3$, too. However, since (meth)acrylate monomer has a property of the rapid heat-curing reaction rate and large hardening shrinkage, it is thought that the cracking generally occurs easy. Even if the general molded product can be employed in order to produce the upper structure, prosthetic material or crown material having small size such as a single crown, double connected crown, or triple connected crown, it is difficult to produce the upper structure, prosthetic material or crown material having bigger size than those. However, when the polymerizable monomer in the moldable material includes the polyethylene glycol dimethacrylate, which has the molecular weight of 300 to 780, in the range of 6 to 30 mass %, it is possible to obtain the dental molded product for milling in big size, as described above. when the dental molded product for milling has big size, it is possible to be used in order to produce from the dental molded product for milling to the upper structure, prosthetic material or crown material having big size and possible to form the crown material like connected crown for full jaw. Additionally, even if the dental molded product has big size, the dental molded product for milling does not occur the cracking easy because of suppressing the heat-curing reaction rate of the moldable material to low and more suppressing the hardening shrinkage at the molding. Consequently, the dental molded product for milling, which has big size, can be obtained with excellent yield.

The polymerizable monomer in the moldable material also preferably includes triethylene glycol dimethacrylate (molecular weight; 286). Especially, in the case that the polymerizable monomer includes polyethylene glycol dimethacrylate having molecular weight of 300 to 780, the polymerizable monomer more preferably includes the triethylene glycol dimethacrylate. In this case, the dental molded product for milling can have excellent strength. The ratio of the triethylene glycol dimethacrylate in the polymerizable monomer is preferably in the range of 1 to 60 mass %. When the ratio of triethylene glycol dimethacrylate is at least 1 mass %, the strength of the dental molded product for milling can be improved. Additionally, when the ratio of the triethylene glycol dimethacrylate is not more than 60 mass %, the total amount of the monomer containing ethylene glycol chains is suppressed. Consequently, the strength of the dental molded product for milling does not become reduced by the water absorption because of suppressing the water absorbency by the ethylene glycol chain. The ratio of triethylene glycol dimethacrylate is more preferably in the range of 20 to 60 mass %.

The content of the polymerizable monomer in the moldable material is preferably in the range of 2 to 49 mass %.

The polymerization initiator can include the well known polymerization initiator such as a thermal initiator and photoinitiator for general dental use. Examples of the polymerization initiator include the thermal initiator such as benzoyl peroxide, tertiary butyl peroxide and methyl ethyl ketone peroxide; and the photoinitiator such as camphorquinone, benzoin and benzophenone. One or multiple species may be selected from the chemical compounds described above.

Example materials of the first spherical inorganic filler and second spherical inorganic filler include silica, alumina and zirconia. Additionally, the materials of the first spherical inorganic filler and second spherical inorganic filler may be, for example, complex ceramics including silica, alumina and zirconia.

The average particle size of the first spherical inorganic filler is in the range of 0.2 to 10 μm, and the moldable composition includes the first spherical inorganic filler in the range of 50 to 85 mass %. Moreover, the average particle size of the second spherical inorganic filler is in the range of 0.005 to 0.1 μm, and the moldable composition includes the second spherical inorganic filler in the range of 1 to 18 mass %. When the particle size distributions of the spherical inorganic fillers are controlled as described above, the moldable composition becomes to have excellent the flowability, the degassing can be allowed in normal pressure, and the molding can be allowed in low or normal pressure. Additionally, the dental molded product for milling formed from the moldable composition becomes to have excellent aesthetic quality and compatibility for machine.

Especially, when the polymerizable monomer includes polyethylene glycol dimethacrylate, which has the molecular weight of 300 to 780, in the range of 6 to 30 mass %, the moldable composition preferably includes the first spherical inorganic filler in the range of 60 to 85 mass %. In this case, the mechanical strength of the molded product tends to reduce in accordance with addition of polyethylene glycol dimethacrylate, but the molded product becomes to have excellent mechanical strength when the content of the first spherical inorganic filler is at least 60 mass %.

Additionally, the average particle size is measured by the laser diffraction method and defined as D50. Herein, D50 means the middle particle size that the accumulation of the volume becomes 50% of total accumulation volume.

Since the first spherical inorganic filler and second spherical inorganic filler have spherical shape, the flowability of moldable composition is improved more, and the surface lubricating property is given to the dental molded product for milling and dental product. Herein, the dental molded product for milling is formed form the moldable composition, and the dental product is obtained by milling the dental molded product for milling. Therefore, when the dental product is mounted within the oral cavity, it is suppressed that the dental product gives damage to the oral cavity and other teeth. Moreover, since the first spherical inorganic filler and second spherical inorganic filler have spherical shape, a wear in milling tool such as drill bit is suppressed at milling the dental molded product for milling.

The first spherical inorganic filler and second spherical inorganic filler need not to be a rigorous spherical object if those surfaces are formed so as to have nearly curved surface. However, from the view that a dispersibility of filler in the moldable composition is improved and the filler is filled in the higher level within the moldable composition, that the transparency of the dental molded product for milling is improved by suppressing a light scattering, and that the wear of milling tool is suppressed at milling the dental molded product for milling, the sphericity of particles of both the first spherical inorganic filler and the second spherical inorganic filler is preferably at least 0.95, more preferably at least 0.96, and yet more preferably at least 0.97. Additionally, the sphericity is, from the surface area of a projected cross-section and the perimeter length of this cross-section of each particle which are obtained based on microphotographic images of the first spherical inorganic filler and the second spherical inorganic filler, the value calculated from (circumferential length of a true circle of the same surface area as the surface area of a particle projection cross-section)/(measurement value of the perimeter length of the particle projection cross-section). The sphericity is defined as average value of values derived for 50 arbitrary particles in each the first spherical inorganic filler and the second spherical inorganic filler.

A surface treatment with a coupling agent may be performed to surfaces of the first spherical inorganic filler and second spherical inorganic filler. In this case, the coupling agent used generally is preferably employed. The coupling agent may be a well-known coupling agent such as gamma-methacryloxypropyl trimethoxysilane and vinyltrimethoxysilane.

The moldable composition may include a well-known additive agent such as polymerization inhibitor, antioxidant, ultraviolet absorber, photostabilizer, antimicrobial agent, fluoride-releasing agent and color pigment. Especially, the additive agent which is included within the moldable composition to obtain the dental material is a suitable chemical compound for the generally dental use.

The dental molded product for milling is formed into a suitable shape such as, for example, prismatic, cylindrical, placoid, or discoid. Additionally, this dental molded product for milling is produced to an artificial tooth; a crown material or prosthetic material such as the crown and inlay for the treatment of a tooth; and an upper structure for the provisional restoration and implant treatment by milling with a CAD/CAM machine. When the dental molded product for milling is cut with the CAD/CAM system for dental use, the uniform prosthetic products are obtained in comparison with manual processing. Additionally, in the case that the prosthetic product for the treatment of a tooth, which is mounted within the oral cavity, has a malfunction such as a chip of a part thereof, it is easy to repair and regenerate the prosthetic products for treatment of a tooth based on a CAD data. Moreover, in the case that the prosthetic product for the treatment of a tooth, which is mounted within the oral cavity, has a chip and the size of chip is so small, since the portion of the chip is filled by using the dental resin material such as past resin for the general dental treatment, the portion of the chip is repaired easy. Herein, since both the prosthetic product and resin material for the treatment of a tooth are made from resin material, the excellent adhesive property express between both of them.

The method to form the dental molded product for milling will be explained as described in below. When a photo irradiation, a heat, or both the photo radiation and heat adapting to the composition is given to the moldable composition, the moldable composition is polymerized and cured. In this way, the dental molded product for milling is obtained.

When the dental molded product for milling is formed from the moldable composition, for example, a molding die may be employed. A material of the molding die is, for example, selected from a metal, ceramics, and a heat-resistant resin. When the moldable composition is cured by the photo irradiation, the molding die may have a portion which enable photo-transmission into the molding die. Herein, the portion is formed, for example, from a glass or PET. The molding die has a cavity of suitable shape such as prismatic, cylindrical, placoid, discoid. Even case that the moldable composition is cured in the normal pressure, in order to suppress the inhibition of polymerization by oxygen, the molding die preferably have structures such as a lid so that the molding die is closed effectively. Additionally, the molding die is previously applied a parting agent to the cavity before molding.

When the moldable composition includes the thermal initiator, for example, after the moldable composition is filled into the cavity of molding die, bubbles are removed from the moldable composition within the cavity in reducing pressure. Next, the moldable composition is polymerized and cured by heating under the applying pressure or normal pressure in the state that the cavity of the molding die is closed by the lid. In this way, the dental molded product for milling is obtained. The pressure level and temperature at the curing may be changed with time in accordance with need. If the moldable composition is heated from room temperature to 100° C. immediately, there is a possibility that the cracking is generated in the dental molded product for milling by heating immediately. Additionally, when the temperature for heating is not more than 100° C., there is a possible that the moldable composition is not cured effectively, that the polymerizable monomer elutes from the dental molded product for milling, and that the effective strength is not given to the dental molded product for milling. Consequently, in the case that the dental molded product for milling is formed by thermal polymerization, for example, the moldable composition is preferably heated under the temperature of not more than 100° C., and then preferably heated under the temperature of 100 to 200° C.

When the moldable composition includes the photo initiator, for example, after the moldable composition is filled into the cavity of molding die, bubbles are removed from the moldable composition within the cavity in reducing pressure. Next, the moldable composition is given the photo irradiation under the applying pressure or normal pressure in the state that the cavity of the molding die is closed by the lid. In this way, the moldable composition is polymerized and cured, and the dental molded product for milling is obtained. At the curing, the heating may be given as an after treatment to the moldable composition after the photo irradiation in accordance with need.

When the polymerizable monomer includes polyethylene glycol dimethacrylate, which has molecular weight of 300 to 780, in the range of 6 to 30 mass %, for example, the molding die for forming the moldable composition has the cavity and lid. In order to obtain the dental molded product for milling of big size, the molding die is prepared. Herein, the molding die has big capacity, for example, in the range of 20 to 350 cm$^3$. After the moldable composition is filled into the cavity of molding die, bubbles are removed from the moldable composition within the cavity in reducing pressure. Next, the moldable composition is polymerized and cured by heating under the applying pressure or normal pressure in the state that the cavity of the molding die is closed by the lid. In this way, the dental molded product for milling is obtained. Although the temperature at the forming is adjusted suitably in accordance with the composition, the temperature is, for example, in the range of 60 to 150° C. Although the pressure given to the moldable composition at the forming is also adjusted suitably, the pressure is, for example, in the range of normal pressure (atmospheric pressure) to 40 MPa. The temperature and pressure at forming may be changed with time in accordance with need.

EXAMPLES

Preparation of the Moldable Composition, and Production of the Molded Product

In each Examples and Comparative Examples, the moldable composition was obtained by mixing the moldable compound shown in Tables 1 to 3. Herein, silane coupling agent, 3EDM, PGA-HMU, TMPTM, and BPO are indicated as gamma-methacryloxypropyltrimethoxysilane, triethyleneglycol dimethacrylate, di(phenylglycidylether acrylate)-hexamethylene diurethane, trimethylolpropane trimethacrylate, and benzoylperoxide, respectively, in Tables 1 to 3.

In Examples 1 to 3, Examples 5 to 7, and Comparative Examples 1 to 7, the moldable composition was filled into the molding die made of stainless. Herein, three kinds of molding dies, which have different cavity size represented as 50 mm×40 mm×2 mm, 50 mm×40 mm×1 mm, and 50 mm×40 mm×5 mm, respectively, were used as the molding die above. And then a stainless lid was fitted onto this molding die after removing bubbles within the moldable composition under the reducing pressure. In this state, the molded product was obtained by heating in first step of the temperature and time shown in Tables 1 to 3, and by heating in second step of the temperature and time shown in Tables 1 to 3.

In Examples 4, the moldable composition was filled into the molding die made of a glass plate and a stainless frame. Herein, two kinds of molding dies, which have different cavity size represented as 50 mm×40 mm×2 mm, 50 mm×40 mm×1 mm, and 50 mm×40 mm×5 mm, respectively, were used as the molding die above. And then a stainless lid was fitted onto this forming die after removing bubbles within the moldable composition under the reducing pressure. In this state, UV light of 356 nm with intensity of 100 mW/cm$^2$ was irradiated for 5 minutes from a dental photopolymerization instrument towards the moldable composition through the glass surface on one side of the molding die, and then the UV light from the dental photopolymerization instrument was irradiated for 5 minutes through the glass surface of the opposite side of the moldable die. Subsequently, the molded product was obtained by heating the moldable composition in the second step of the temperature and time shown in Tables 1 to 3.

The test piece was cut out from the molded product obtained in each of the Examples and comparative Examples. Evaluation tests for each of these pieces were carried out by methods described in below.

(Moldability)

The theoretical specific gravity value was calculated based on the specific gravity of the molded product obtained from a composition removed the inorganic filler in the moldable composition and the true specific gravity of the inorganic filler. The evaluation was judged as "good" when the difference of the theoretic value of specific gravity and the measured value of specific gravity of the molded product was less than 0.03, and was judged as "irrelevant" when the difference described above was 0.03 and more. This result becomes as an indicator for the degree of void generation in the molded product.

(Test of Bending Strength in Normal State)

The dimension of the test piece was defined as 25 mm×2 mm×2 mm, and the strength at break of this test piece was measured in a crosshead speed of 1 mm per minute using a bending testing machine. In each Examples and Comparative Examples, the measurement for each five test pieces was performed, and the evaluation was performed according to the average value of the results. The evaluated value was decided as a central value representing the strength of the molded product.

(Test of Bending Strength after Water Immersion)

The dimension of the test piece was defined as 25 mm×2 mm×2 mm, and the test piece was immersed in the water kept at 37° C. for 24 hours. Next, the strength at break of the test piece was measured in a crosshead speed of 1 mm per minute using a bending testing machine. In each Examples and Comparative Examples, the measurement for each five test pieces was performed, and the evaluation was performed according to the average value of the results. The evaluated value was decided as a central value representing the strength of the molded product.

(Transparency)

The dimensions of the test piece were 13 mm×13 mm×1 mm. The buffing was performed to the test piece until the test piece has a thickness of 0.8 mm. The photo-transmittance of the air was defined as 100%, and the photo-transmittance of test piece was measured with a hazemeter. In each Examples and Comparative Examples, the measurement for each three test pieces was performed, and the evaluation was performed according to the average value of the results. The evaluated value was decided as a central value representing the aesthetic quality of the molded product.

(Drill Wearability)

The dimension of the test piece was defined as the planar view of 50 mm×40 mm and the thickness of 5 mm. The penetration processes of 1,000 times were performed using a carbide drill, which has a diameter of 1 mm and the flute length of 15 mm, at the revolution speed of 10,000 per min and the feed speed of 500 mm/min so as to pass through the test piece in thickness direction thereof. Herein, a edge area of the carbide drill was observed before and after the process. The drill wearability was evaluated according to a value of the ratio (the edge area after the penetration process/the edge area before the penetration process). The value was decided as a central value representing the formability of the molded product.

(Evaluation Results)

The above results are shown in the following Tables 1 to 3.

TABLE 1

| | | | Example | | | | | |
|---|---|---|---|---|---|---|---|---|
| | | | 1 | 2 | 3 | 4 | 5 | 6 |
| Composition | Inorganic filler | Species | spherical fused silica | spherical fused silica | spherical fused silica | spherical fused silica | spherical fused silica | spherical fused silica |
| | | Average particle size (μm) | 0.6 | 0.6 | 0.6 | 0.6 | 0.6 | 0.6 |
| | | Sphericity | 0.98 | 0.98 | 0.98 | 0.98 | 0.98 | 0.98 |
| | | Content (parts by mass) | 55 | 60 | 65 | 60 | 60 | 65 |
| | Inorganic filler | Species | spherical fused silica | spherical fused silica | spherical fused silica | spherical fused silica | spherical fused silica | spherical fused silica |
| | | Average | 0.050 | 0.050 | 0.050 | 0.050 | 0.050 | 0.050 |

TABLE 1-continued

|  |  |  | Example | | | | | |
|---|---|---|---|---|---|---|---|---|
|  |  |  | 1 | 2 | 3 | 4 | 5 | 6 |
|  |  | particle size (μm) |  |  |  |  |  |  |
|  |  | Sphericity | 0.98 | 0.98 | 0.98 | 0.98 | 0.98 | 0.98 |
|  |  | Content (parts by mass) | 15 | 10 | 5 | 10 | 10 | 10 |
|  | silane coupling agent | Content (parts by mass) | 0.3 | 0.3 | 0.3 | 0.3 | 0.3 | 0.3 |
|  | 3EDM | Content (parts by mass) | 20 | 20 | 20 | 20 | 14 | 15 |
|  | PGA-HMU | Content (parts by mass) | 10 | 10 | 10 | 10 | 13 | 10 |
|  | TMPTM | Content (parts by mass) | 0 | 0 | 0 | 0 | 13 | 0 |
|  | BPO | Content (parts by mass) | 0.5 | 0.5 | 0.5 | 0 | 0.5 | 0.5 |
|  | Camphorquinone | Content (parts by mass) | 0 | 0 | 0 | 0.5 | 0 | 0 |
| Molding condition | Pressure |  | normal pressure | normal pressure | normal pressure | normal pressure | normal pressure | 10 MPa |
|  | Temperature, time and the like | First step | 80° C., 1 hour | 80° C., 1 hour | 80° C., 1 hour | UV light irradiation | 80° C., 1 hour | 80° C., 1 hour |
|  |  | Second step | 120° C., 2 hours | 120° C., 2 hours | 120° C., 2 hours | 120° C., 30 minutes | 120° C., 2 hours | 120° C., 2 hours |
| Evaluation result | Moldability |  | good | good | good | good | good | good |
|  | Test of the bending strength in normal state (MPa) |  | 162 | 163 | 167 | 165 | 164 | 168 |
|  | Test of the bending strength after water immersion (MPa) |  | 146 | 153 | 155 | 150 | 155 | 158 |
|  | Transparency |  | 58 | 55 | 52 | 57 | 60 | 52 |
|  | Drill wearability |  | 0.97 | 0.96 | 0.93 | 0.94 | 0.95 | 0.92 |

TABLE 2

|  |  |  | Example | | | Comparative Example | |
|---|---|---|---|---|---|---|---|
|  |  |  | 7 | 8 | 9 | 1 | 2 |
| Composition | Inorganic filler | Species | spherical fused silica | spherical fused silica | spherical fused silica | spherical fused silica | spherical fused silica |
|  |  | Average particle size (μm) | 1.5 | 10 | 6 | 0.6 | 1.5 |
|  |  | Sphericity | 0.97 | 0.97 | 0.98 | 0.98 | 0.97 |
|  |  | Content (parts by mass) | 60 | 77 | 85 | 55 | 40 |
|  | Inorganic filler | Species | spherical fused silica | spherical fused silica | spherical fused silica | spherical fused silica | spherical fused silica |
|  |  | Average particle size | 0.015 | 0.100 | 0.050 | 0.050 | 0.015 |

TABLE 2-continued

| | | | Example | | | Comparative Example | |
|---|---|---|---|---|---|---|---|
| | | | 7 | 8 | 9 | 1 | 2 |
| | | (μm) | | | | | |
| | | Sphericity | 0.99 | 0.98 | 0.98 | 0.98 | 0.99 |
| | | Content (parts by mass) | 10 | 5 | 5 | 25 | 25 |
| | silane coupling agent | Content (parts by mass) | 0.3 | 0.3 | 0.3 | 0.3 | 0.3 |
| | 3EDM | Content (parts by mass) | 20 | 9 | 5 | 10 | 20 |
| | PGA-HMU | Content (parts by mass) | 10 | 9 | 5 | 10 | 15 |
| | TMPTM | Content (parts by mass) | 0 | 0 | 0 | 0 | 0 |
| | BPO | Content (parts by mass) | 0.5 | 0.5 | 0.5 | 0.5 | 0.5 |
| | Camphorquinone | Content (parts by mass) | 0 | 0 | 0 | 0 | 0 |
| Molding condition | Pressure | | normal pressure | 10 MPa | 30 MPa | normal pressure | 30 MPa |
| | Temperature, time and the like | First step | 80° C., 1 hour | 80° C., 1 hour | 80° C., 1 hour | 80° C., 1 hour | 80° C., 1 hour |
| | | Second step | 120° C., 2 hours | 120° C., 2 hours | 120° C., 2 hours | 120° C., 2 hours | 120° C., 2 hours |
| Evaluation result | Moldability | | good | good | good | irrelevant | good |
| | Test of the bending strength in normal state (MPa) | | 170 | 175 | 194 | — | 98 |
| | Test of the bending strength after water immersion (MPa) | | 154 | 163 | 188 | — | 79 |
| | Transparency | | 52 | 50 | 50 | — | 60 |
| | Drill wearability | | 0.95 | 0.90 | 0.90 | — | 0.97 |

TABLE 3

| | | | Comparative Example | | | | |
|---|---|---|---|---|---|---|---|
| | | | 3 | 4 | 5 | 6 | 7 |
| Composition | Inorganic filler | Species | spherical fused silica | spherical fused silica | spherical fused silica | crushed and fused silica | crushed and fused silica |
| | | Average particle size (μm) | 0.15 | 20 | 10 | 10 | 10 |
| | | Sphericity | 0.98 | 0.97 | 0.97 | — | — |
| | | Content (parts by mass) | 60 | 60 | 88 | 70 | 50 |
| | Inorganic filler | Species | — | spherical fused silica | spherical fused silica | spherical fused silica | spherical fused silica |
| | | Average particle size (μm) | — | 0.050 | 0.100 | 0.100 | 0.100 |
| | | Sphericity | — | 0.98 | 0.98 | 0.98 | 0.98 |
| | | Content (parts by mass) | — | 10 | 4 | 5 | 5 |
| | silane coupling agent | Content (parts by mass) | 0.3 | 0.3 | 0.3 | 0.3 | 0.3 |
| | 3EDM | Content | 20 | 20 | 4 | 15 | 25 |

TABLE 3-continued

|  |  |  | Comparative Example | | | | |
|---|---|---|---|---|---|---|---|
|  |  |  | 3 | 4 | 5 | 6 | 7 |
|  | PGA-HMU | (parts by mass) Content (parts by mass) | 20 | 10 | 4 | 10 | 20 |
|  | TMPTM | Content (parts by mass) | 0 | 0 | 0 | 0 | 0 |
|  | BPO | Content (parts by mass) | 0.5 | 0.5 | 0.5 | 0.5 | 0.5 |
|  | Camphorquinone | Content (parts by mass) | 0 | 0 | 0 | 0 | 0 |
| Molding condition | Pressure |  | 30 MPa | normal pressure | 30 MPa | 30 MPa | 30 MPa |
|  | Temperature, time and the like | First step | 80° C., 1 hour | 80° C., 1 hour | 80° C., 1 hour | 80° C., 1 hour | 80° C., 1 hour |
|  |  | Second step | 120° C., 2 hours | 120° C., 2 hours | 120° C., 2 hours | 120° C., 2 hours | 120° C., 2 hours |
| Evaluation result | Moldability |  | good | good | irrelevant | irrelevant | good |
|  | Test of the bending strength in normal state (MPa) |  | 105 | 142 | — | — | 158 |
|  | Test of the bending strength after water immersion (MPa) |  | 86 | 132 | — | — | 144 |
|  | Transparency |  | 56 | 47 | — | — | 48 |
|  | Drill wearability |  | 0.97 | 0.75 | — | — | 0.71 |

According to these results, Examples 1 to 9 indicate that the moldable composition has excellent moldability because the void does not generate easy at molding, that the molded product has the excellent mechanical strength because of high bending strength, and that the molded product has higher transparency and lower drill wearability, comparing to Comparative Examples 1 to 7.

Examples 10 to 22, Comparative Examples 8 to 10

Preparations of Materials for Molding and Production of Molded Product

In each Example and Comparative Example, materials for molding were obtained by mixing the compounds shown in Tables 4 to 9 below. In Table 4 to 9, silane coupling agent, 3EDM, 4EDM, 9EDM, 14EDM, PGA-HMU, NPGDM, TMPTM, and BPO are represented as gamma-methacryloxypropyltrimethoxysilane, triethyleneglycol dimethacrylate, tetraethyleneglycol dimethacrylate, nonaethyleneglycol dimethacrylate, tetradecaethyleneglycol dimethacrylate, di(phenylglycidylether acrylate)-hexamethylene diurethane, Neopentanediol dimethacrylate, trimethylolpropane trimethacrylate, and benzoylperoxide, respectively.

Each moldable compositions was filled into the molding die of stainless. Herein, the molding die has a cavity size represented as the diameter of 5 cm, the thickness of 2 cm and the capacity of 39.3 cm³. A stainless lid was fitted onto this molding die after removing bubbles within the moldable composition under the reducing pressure. In this state, the moldable composition was heated at 60° C. for 3 hours under normal pressure, and then heated at 120° C. for 2 hours. In this way, the dental molded product for milling was obtained.

(Moldability)

The moldability was evaluated with the same method as Examples 1 to 9 and Comparative Example 1 to 7.

(Evaluation of Cracking)

In each Example and Comparative Example, ten dental molded products for milling were obtained by repeating ten times molding of the moldable composition. The appearance of the dental molded product for milling was observed visually. When at least one of the dental molded product having cracking was included in ten dental molded products, the evaluation was judged as "irrelevant". Other hand, when the cracking was not found in all of the dental molded products, the evaluation was judged as "good".

(Evaluation of Bending Strength in Normal State)

The bending strength in normal state was evaluated with the same method as Examples 1 to 9 and Comparative Example 1 to 7.

(Evaluation of Bending Strength after Water Immersion)

The bending strength after water immersion was evaluated with the same method as Examples 1 to 9 and Comparative Example 1 to 7.

(Transparency)

The transparency was evaluated with the same method as Examples 1 to 9 and Comparative Example 1 to 7.

TABLE 4

| | | | Example | | | | | |
|---|---|---|---|---|---|---|---|---|
| | | | 10 | 11 | 12 | 13 | 14 | 15 |
| Composition | Inorganic filler | Species | spherical fused silica | spherical fused silica | spherical fused silica | spherical fused silica | spherical fused silica | spherical fused silica |
| | | Average particle size (μm) | 0.6 | 0.6 | 0.6 | 0.6 | 0.6 | 0.6 |
| | | Sphericity | 0.98 | 0.98 | 0.98 | 0.98 | 0.98 | 0.98 |
| | | Content (parts by mass) | 70 | 75 | 75 | 75 | 70 | 61 |
| | Inorganic filler | Species | spherical fused silica | spherical fused silica | spherical fused silica | spherical fused silica | spherical fused silica | spherical fused silica |
| | | Average particle size (μm) | 0.050 | 0.050 | 0.050 | 0.050 | 0.050 | 0.050 |
| | | Sphericity | 0.98 | 0.98 | 0.98 | 0.98 | 0.98 | 0.98 |
| | | Content (parts by mass) | 10 | 10 | 10 | 9 | 10 | 10 |
| | silane coupling agent | Content (parts by mass) | 0.4 | 0.4 | 0.4 | 0.4 | 0.4 | 0.4 |
| | 3EDM | Content (parts by mass) | 8 | 8 | 8 | 7 | 7 | 12 |
| | 4EDM | Content (parts by mass) | 0 | 0 | 0 | 0 | 6 | 0 |
| | 9EDM | Content (parts by mass) | 4 | 2 | 2 | 0 | 0 | 5 |
| | 14EDM | Content (parts by mass) | 0 | 0 | 0 | 1 | 0 | 0 |
| | PGA-HMU | Content (parts by mass) | 8 | 0 | 0 | 0 | 7 | 0 |
| | NPGDM | Content (parts by mass) | 0 | 5 | 0 | 8 | 0 | 12 |
| | TMPTM | Content (parts by mass) | 0 | 0 | 5 | 0 | 0 | 0 |
| | BPO | Content (parts by mass) | 0.4 | 0.4 | 0.4 | 0.4 | 0.4 | 0.6 |

TABLE 5

| | | | Example | | | | | |
|---|---|---|---|---|---|---|---|---|
| | | | 10 | 11 | 12 | 13 | 14 | 15 |
| Molding condition | Pressure | | normal pressure | normal pressure | normal pressure | normal pressure | normal pressure | normal pressure |
| | Temperature, time and the like | First step | 60° C., 3 hours | 60° C., 3 hours | 60° C., 3 hours | 60° C., 3 hours | 60° C., 3 hours | 60° C., 3 hours |
| | | Second step | 80° C., 1 hour | 80° C., 1 hour | 80° C., 1 hour | 80° C., 1 hour | 80° C., 1 hour | 80° C., 1 hour |

TABLE 5-continued

| | | | Example | | | | | |
|---|---|---|---|---|---|---|---|---|
| | | | 10 | 11 | 12 | 13 | 14 | 15 |
| | | Third step | 120° C., 2 hours | 120° C., 2 hours | 120° C., 2 hours | 120° C., 2 hours | 120° C., 2 hours | 120° C., 2 hours |
| Ratio of composition | Percentage of "polyethylene glycol dimethacrylate having a molecular weight of 300 to 780" to total mass of polymerizable monomer (mass %) | | 20 | 13 | 13 | 6 | 30 | 17 |
| | Percentage of Triethylene glycol dimethacrylate to total mass of polymerizable monomer (mass %) | | 40 | 53 | 53 | 44 | 35 | 41 |
| | Percentage of first inorganic filler to total mass of materials for molding (mass %) | | 69 | 74 | 74 | 74 | 69 | 60 |
| | Percentage of second inorganic filler to total mass of materials for molding (mass %) | | 10 | 10 | 10 | 9 | 10 | 10 |
| Evaluation | Moldability | | good | good | good | good | good | Good |
| | Evaluation of cracking | | good | good | good | good | good | good |
| | Evaluation of bending strength in normal state [MPa] | | 170 | 174 | 179 | 172 | 175 | 161 |
| | Evaluation of bending strength after water immersion [MPa] | | 162 | 164 | 168 | 160 | 164 | 147 |
| | Transparency | | 45 | 60 | 58 | 58 | 46 | 55 |

TABLE 6

| | | | Example | | | | |
|---|---|---|---|---|---|---|---|
| | | | 16 | 17 | 18 | 19 | 20 |
| Composition | Inorganic filler | Species | spherical fused silica | spherical fused silica | spherical fused silica | spherical fused silica | spherical fused silica |
| | | Average particle size (μm) | 0.6 | 0.6 | 0.6 | 0.6 | 0.6 |
| | | Sphericity | 0.98 | 0.98 | 0.98 | 0.98 | 0.98 |
| | | Content (parts by mass) | 85 | 75 | 85 | 62 | 70 |
| | Inorganic filler | Species | spherical fused silica | spherical fused silica | spherical fused silica | spherical fused silica | spherical fused silica |
| | | Average particle size (μm) | 0.050 | 0.050 | 0.050 | 0.050 | 0.050 |
| | | Sphericity | 0.98 | 0.98 | 0.98 | 0.98 | 0.98 |
| | | Content (parts by mass) | 5 | 10 | 1 | 18 | 10 |
| | silane coupling agent | Content (parts by mass) | 0.3 | 0.4 | 0.4 | 0.4 | 0.4 |

TABLE 6-continued

|  |  |  | Example |  |  |  |  |
|---|---|---|---|---|---|---|---|
|  |  |  | 16 | 17 | 18 | 19 | 20 |
|  | 3EDM | Content (parts by mass) | 6 | 0 | 7 | 8 | 10 |
|  | 4EDM | Content (parts by mass) | 2 | 4 | 0 | 0 | 0 |
|  | 9EDM | Content (parts by mass) | 0 | 0 | 2 | 4 | 1 |
|  | 14EDM | Content (parts by mass) | 0 | 0 | 0 | 0 | 0 |
|  | PGA-HMU | Content (parts by mass) | 0 | 0 | 0 | 0 | 9 |
|  | NPGDM | Content (parts by mass) | 2 | 6 | 5 | 8 | 0 |
|  | TMPTM | Content (parts by mass) | 0 | 5 | 0 | 0 | 0 |
|  | BPO | Content (parts by mass) | 0.2 | 0 | 0.4 | 0.4 | 0.4 |

TABLE 7

|  |  |  | Example |  |  |  |  |
|---|---|---|---|---|---|---|---|
|  |  |  | 16 | 17 | 18 | 19 | 20 |
| Molding condition | Pressure |  | normal pressure | normal pressure | normal pressure | normal pressure | normal pressure |
|  | Temperature, time and the like | First step | 60° C., 3 hours | 60° C., 3 hours | 60° C., 3 hours | 60° C., 3 hours | 60° C., 3 hours |
|  |  | Second step | 80° C., 1 hour | 80° C., 1 hour | 80° C., 1 hour | 80° C., 1 hour | 80° C., 1 hour |
|  |  | Third step | 120° C., 2 hours | 120° C., 2 hours | 120° C., 2 hours | 120° C., 2 hours | 120° C., 2 hours |
| Ratio of composition | Percentage of "polyethylene glycol dimethacrylate having a molecular weight of 300 to 780" to total mass of polymerizable monomer (mass %) |  | 20 | 27 | 14 | 20 | 5 |
|  | Percentage of Triethylene glycol dimethacrylate to total mass of polymerizable monomer (mass %) |  | 60 | 0 | 50 | 40 | 50 |
|  | Percentage of first inorganic filler to total mass of materials for molding (mass %) |  | 85 | 74 | 84 | 62 | 69 |
|  | Percentage of second inorganic filler to total mass of materials for molding (mass %) |  | 5 | 10 | 1 | 18 | 10 |
| Evaluation | Moldability |  | good | good | good | good | good |
|  | Evaluation of cracking |  | good | good | good | good | irrelevant |
|  | Evaluation of bending strength in normal state [MPa] |  | 203 | 172 | 168 | 165 | 180 |

TABLE 7-continued

| | Example | | | | |
|---|---|---|---|---|---|
| | 16 | 17 | 18 | 19 | 20 |
| Evaluation of bending strength after water immersion [MPa] | 196 | 161 | 160 | 150 | 171 |
| Transparency | 57 | 52 | 43 | 62 | 53 |

TABLE 8

| | | | Example | | Comparative Example | | |
|---|---|---|---|---|---|---|---|
| | | | 21 | 22 | 8 | 9 | 10 |
| Composition | Inorganic filler | Species | spherical fused silica | spherical fused silica | spherical fused silica | spherical fused silica | spherical fused silica |
| | | Average particle size (μm) | 0.6 | 0.6 | 0.6 | 0.6 | 0.6 |
| | | Sphericity | 0.98 | 0.98 | 0.98 | 0.98 | 0.98 |
| | | Content (parts by mass) | 70 | 70 | 90 | 80 | 61 |
| | Inorganic filler | Species | spherical fused silica | spherical fused silica | spherical fused silica | spherical fused silica | spherical fused silica |
| | | Average particle size (μm) | 0.050 | 0.050 | 0.050 | 0.050 | 0.050 |
| | | Sphericity | 0.98 | 0.98 | 0.98 | 0.98 | 0.98 |
| | | Content (parts by mass) | 10 | 10 | 1 | 0 | 20 |
| | silane coupling agent | Content (parts by mass) | 0.4 | 0.4 | 0.4 | 0.4 | 0.4 |
| | 3EDM | Content (parts by mass) | 7 | 13 | 4 | 8 | 8 |
| | 4EDM | Content (parts by mass) | 0 | 0 | 2 | 0 | 0 |
| | 9EDM | Content (parts by mass) | 7 | 4 | 0 | 4 | 4 |
| | 14EDM | Content (parts by mass) | 0 | 0 | 0 | 0 | 0 |
| | PGA-HMU | Content (parts by mass) | 6 | 3 | 3 | 8 | 7 |
| | NPGDM | Content (parts by mass) | 0 | 0 | 0 | 0 | 0 |
| | TMPTM | Content (parts by mass) | 0 | 0 | 0 | 0 | 0 |
| | BPO | Content (parts by mass) | 0.4 | 0.4 | 0.1 | 0.4 | 0.4 |

TABLE 9

|  |  |  | Example | | Comparative Example | | |
|---|---|---|---|---|---|---|---|
|  |  |  | 21 | 22 | 8 | 9 | 10 |
| Molding condition | Pressure |  | normal pressure | normal pressure | normal pressure | normal pressure | normal pressure |
|  | Temperature, time and the like | First step | 60° C., 3 hours | 60° C., 3 hours | 60° C., 3 hours | 60° C., 3 hours | 60° C., 3 hours |
|  |  | Second step | 80° C., 1 hour | 80° C., 1 hour | 80° C., 1 hour | 80° C., 1 hour | 80° C., 1 hour |
|  |  | Third step | 120° C., 2 hours | 120° C., 2 hours | 120° C., 2 hours | 120° C., 2 hours | 120° C., 2 hours |
| Ratio of composition | Percentage of "polyethylene glycol dimethacrylate having a molecular weight of 300 to 780" to total mass of polymerizable monomers (mass %) |  | 35 | 20 | 22 | 20 | 21 |
|  | Percentage of Triethylene glycol dimethacrylate to total mass of polymerizable monomer (mass %) |  | 35 | 65 | 44 | 40 | 42 |
|  | Percentage of first inorganic filler to total mass of materials for molding (mass %) |  | 69 | 69 | 90 | 79 | 61 |
|  | Percentage of second inorganic filler to total mass of materials for molding (mass %) |  | 10 | 10 | 1 | 0 | 20 |
| Evaluation | Moldability |  | good | good | irrelevant | good | irrelevant |
|  | Evaluation of cracking |  | good | irrelevant | — | good | — |
|  | Evaluation of bending strength in normal state [MPa] |  | 150 | 171 | — | 135 | — |
|  | Evaluation of bending strength after water immersion [MPa] |  | 140 | 157 | — | 124 | — |
|  | Transparency |  | 40 | 47 | — | 20 | — |

According to these results, Examples 10 to 22 indicate that the moldable composition has excellent moldability because the void does not generate easy at molding, that the molded product has the excellent mechanical strength because of high bending strength, and that the molded product has higher transparency, comparing to Comparative Examples 8 to 10.

Additionally, in Examples 10 to 19, the dental molded product has more excellent mechanical strength, and the cracking did not generate easy at the molding the moldable composition. Therefore, it is evaluated that Examples 10 to 19 can be applied in order to produce the dental molded product for milling in big size.

The invention claimed is:

1. A dental molded product for milling,
wherein said dental molded product for milling is obtained by curing a moldable composition,
wherein said moldable composition comprises;
a polymerizable monomer,
a polymerization initiator,
a first spherical inorganic filler, and
a second spherical inorganic filler,
wherein said first spherical inorganic filler has an average particle size in the range of 0.2 to 10 μm and is included in a content of 60 to 85 mass %,
wherein said second spherical inorganic filler has an average particle size in the range of 0.005 to 0.1 μm and is included in a content of 1 to 18 mass %, and
wherein said polymerizable monomer comprises a polyethylene glycol dimethacrylate in the range of 6 to 30 mass %, said polyethylene glycol dimethacrylate having a molecular weight in the range of 300 to 780.

2. The dental molded product for milling according to claim 1, wherein said polymerizable monomer further comprises a triethylene glycol dimethacrylate in a content of 1 to 60 mass %.

3. A manufactural method of the dental molded product for milling according to claim 1, wherein said manufactural method comprises;
a preparation process of preparing the moldable composition,
a filling process of filling the moldable composition in a molding die,
a degassing process of degassing the moldable composition with a decompression in the molding die, and
a curing process of curing the moldable composition in the molding die under a pressure of a normal pressure to 40 MPa.

4. A manufactural method of the dental molded product for milling according to claim 2, wherein said manufactural method comprises;
- a preparation process of preparing the moldable composition,
- a filling process of filling the moldable composition in a molding die,
- a degassing process of degassing the moldable composition with a decompression in the molding die, and
- a curing process of curing the moldable composition in the molding die under a pressure of a normal pressure to 40 MPa.

5. A manufactural method of the dental molded product for milling according to claim 3, wherein said manufactural method comprises;
- a preparation process of preparing the moldable composition,
- a filling process of filling the moldable composition in a molding die,
- a degassing process of degassing the moldable composition with a decompression in the molding die, and
- a curing process of curing the moldable composition in the molding die under a pressure of a normal pressure to 40 MPa.

* * * * *